United States Patent [19]

Kiema et al.

[11] Patent Number: 5,984,966
[45] Date of Patent: *Nov. 16, 1999

[54] BIOABSORBABLE BONE BLOCK FIXATION IMPLANT

[75] Inventors: Pia Kiema; Petteri Kousa; Markku Järvinen; Auvo Kaikkonen, all of Tampere, Finland; Mark Sherman, New York, N.Y.; Jyri Öhrling; Pertti Törmälä, both of Tampere, Finland

[73] Assignee: Bionx Implants OY, Tampere, Finland

[*] Notice: This patent issued on a continued prosecution application filed under 37 CFR 1.53(d), and is subject to the twenty year patent term provisions of 35 U.S.C. 154(a)(2).

[21] Appl. No.: 09/033,475

[22] Filed: Mar. 2, 1998

[51] Int. Cl.$^6$ .......................................................... A61F 2/08
[52] U.S. Cl. ................................................................ 623/13
[58] Field of Search ........................................ 623/13, 16

[56] References Cited

U.S. PATENT DOCUMENTS

| | | | |
|---|---|---|---|
| 4,744,793 | 5/1988 | Parr | 623/13 |
| 4,968,317 | 11/1990 | Törmälä et al. | |
| 4,997,433 | 3/1991 | Goble | 623/13 |
| 5,080,663 | 1/1992 | Mills et al. | |
| 5,108,431 | 4/1992 | Mansat | 623/13 |
| 5,234,430 | 8/1993 | Huebner | |
| 5,282,802 | 2/1994 | Mahoney, III | |
| 5,356,435 | 10/1994 | Thein | 623/13 |
| 5,360,448 | 11/1994 | Thramann | |
| 5,383,878 | 1/1995 | Roger et al. | |
| 5,405,359 | 4/1995 | Pierce | |
| 5,425,767 | 6/1995 | Steininger | 623/13 |
| 5,454,811 | 10/1995 | Huebner | |
| 5,470,334 | 11/1995 | Ross et al. | |
| 5,632,748 | 5/1997 | Beck, Jr. et al. | |
| 5,766,250 | 6/1998 | Chervitz | 623/13 |

FOREIGN PATENT DOCUMENTS

| | | |
|---|---|---|
| 0 146 398 A2 | 6/1985 | European Pat. Off. |
| 0 464 479 A1 | 1/1992 | European Pat. Off. |
| 0 611 557 A2 | 8/1994 | European Pat. Off. |
| 0 464 479 B1 | 3/1995 | European Pat. Off. |
| 0 651 979 A1 | 5/1995 | European Pat. Off. |
| 2 307 179 | 5/1997 | United Kingdom |
| WO 90 04982 | 5/1990 | WIPO |
| WO 92 03980 | 3/1992 | WIPO |
| WO 96 41596 | 12/1996 | WIPO |

OTHER PUBLICATIONS

Bach, B.R., Potential Pitfalls of Kurosaka Screw Interference for ACL Surgery, American Journal of Knee Surgery, vol. 2 No. 2 (1989) at 76–82.

Barber, A.F., Burton, E.F., McGuire, D.A. and Paulos, L.E., Preliminary Results of an Absorbable Interference Screw, The Journal of Arthoscopic and Related Surgery, vol. 11, No. 5 (1995) at 537–548.

Bach, B.R., Arthroscopy–Assisted Patellar Tendon Substitution for Anterior Cruciate Ligament Insufficiency, American Journal of Knee Surgery, vol. 2, No. 1 (1989) at 3–20.

Daniel, D.M., Akeson, W.H., O'Connor, J.J. (eds.): Knee Ligaments Structure, Function, Injury and Repair, New York Raven Press, 1990 at 11–29.

Kurosoka M., Yoshiya S, Andrish JT: A Biomechanical Comparison of Different Surgical Techniques of Graft Fixation in Anterior Cruciate Ligaments Reconstruction, Am. J. Sports Med. 15 (1987) at 225–229.

Rupp, S., Krauss, P.W. and Fritsch, E.W., Fixation Strength of a Biodegradable Interference Screw and a Press–Fit Technique in Anterior Cruciate Ligament Reconstruction with a BPTB Graft, Journal of Arthroscopic and Related Surgery, vol. 13, No. 1 (1997) at 61–65.

Vainionpää, S., Rokkanen, P. and Törmälä, P., Surgical Applications of Biodegreadable Polymers in Human Tissues, Progr. Polym. Sci., vol. 14 (1989) at 679–716.

Medical Data International, Inc. Orthopedic and Musculoskeletal Markets: Biotechnology and Tissue Engineering, Feb. 1997 at ES 1–18 and 1–28.

Primary Examiner—Michael J. Milano
Attorney, Agent, or Firm—Kenyon & Kenyon

[57] ABSTRACT

The invention relates to pliable surgical implants manufactured of bioabsorbable (or biodegradable) polymer, copolymer, polymer alloy or composite and used for fixation of a bone block (graft) into a drillhole in a bone.

12 Claims, 3 Drawing Sheets

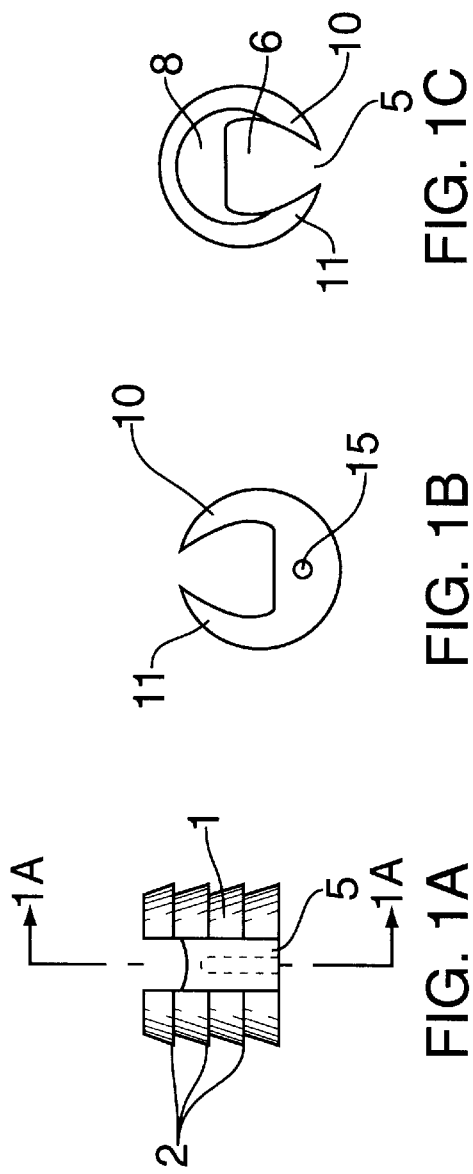
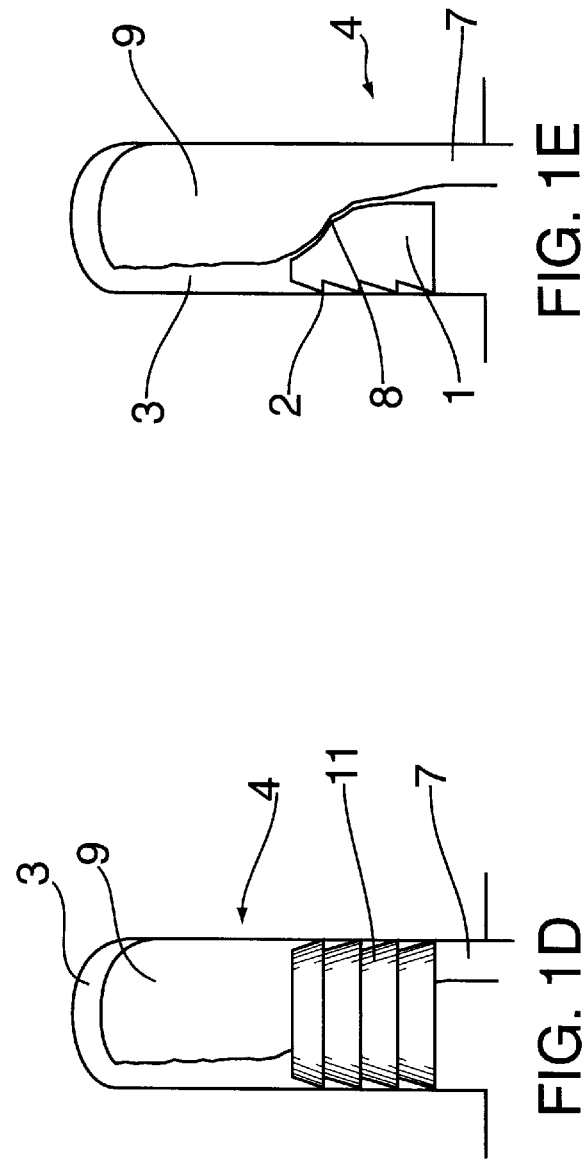

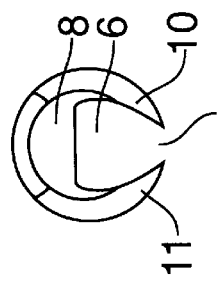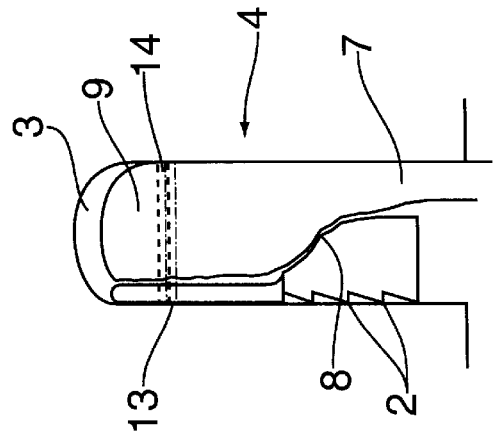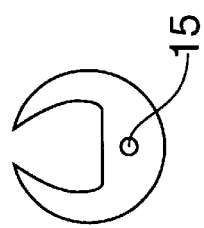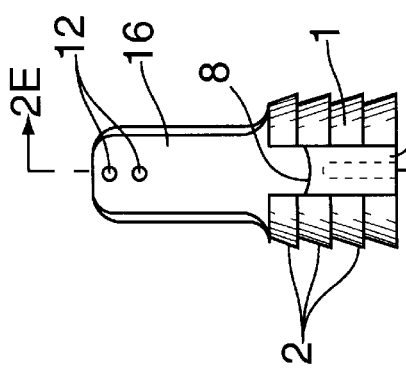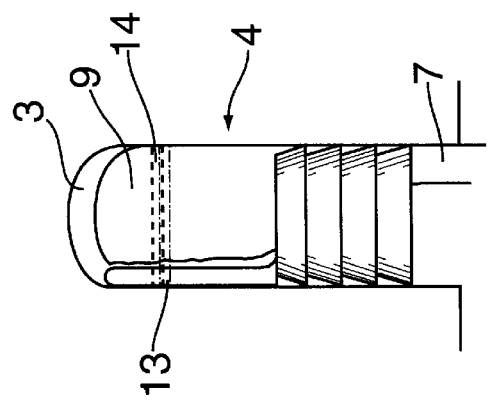

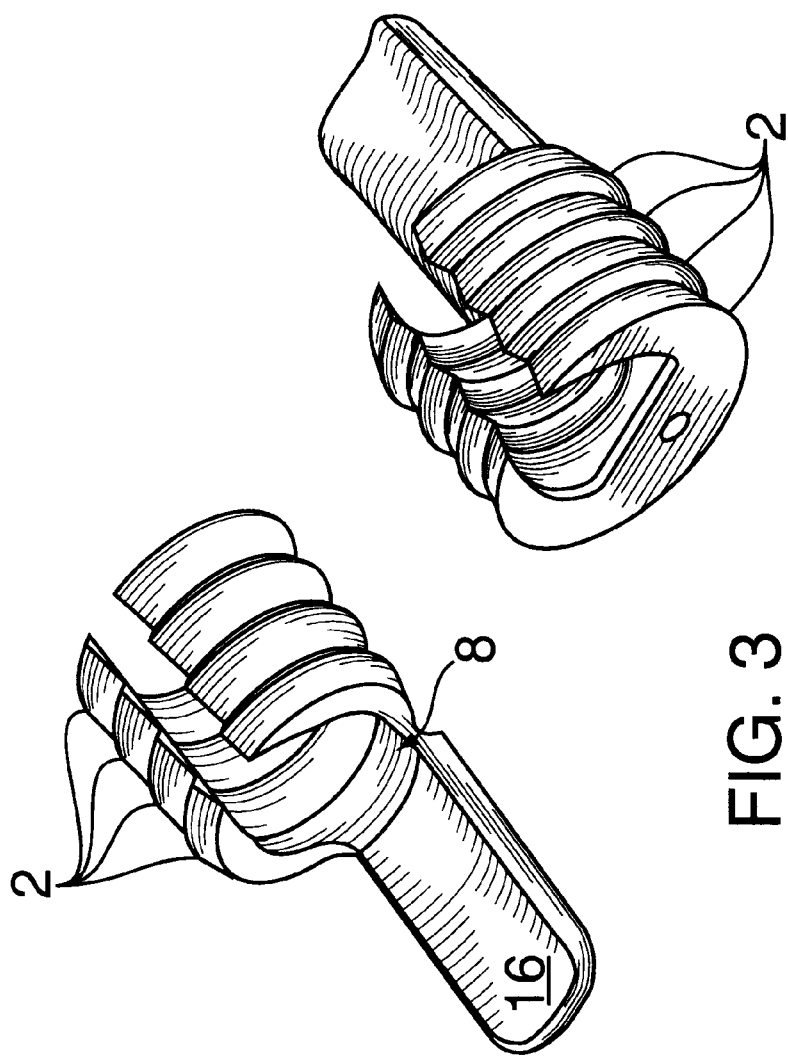
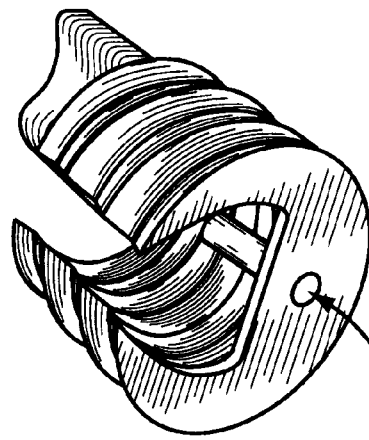
FIG. 3
FIG. 4

BIOABSORBABLE BONE BLOCK FIXATION IMPLANT

BACKGROUND OF THE INVENTION

The invention relates to surgical implants manufactured of bioabsorbable (or biodegradable) polymer, copolymer, polymer alloy or composite and used for fixation of a bone block (graft) into a drillhole in a bone.

DESCRIPTION OF THE PRIOR ART

In surgery it is generally known to use a bone-patellar tendon-bone (BPTB) graft, taken from the knee of the patient, to replace the severely damaged anterior cruciate ligament (ACL). In a surgical procedure one bone graft is fixed into a drillhole made from the knee joint into the distal femur and another bone graft is fixed into a drillhole made into the proximal tibia. The bone plugs are fixed into drillholes with bone fixation screws and in most cases with so-called interference screws. A screw is installed into the space between the drillhole and the bone graft to lock the bone graft into the drillhole. The patellar tendon part between the bone blocks acts as a new ACL. The surgical technique of such bone-tendon-bone procedures is described, e.g., in Bach, B. R., Potential Pitfalls of Kurosaka Screw Interference Fixation for ACL Surgery, The American Journal of Knee Surgery, Vol. 2, No, 2 (1989), at 76–82, the entire disclosure of which is incorporated herein by way of this reference.

The fixation screws, like interference screws, are normally made of metal, like stainless steel or titanium or of a bioabsorbable polymer, like polylactide. Metallic and/or bioabsorbable polymeric materials and composites, suitable for manufacturing of bone-tendon-bone graft fixation screws, are described in literature, like in Barber, A. F., Burton, E. F., McGuire, D. A. and Paulos L. E., Preliminary Results of an Absorbable Interference Screw, The Journal of Arthroscopic and Related Surgery, Vol. 11, No. 5 (1995), at 537–548; Sèquin, F. and Texhammer, R., ASIF/AO Instrumentation, Springer-Verlag, Berlin Heidelberg New York 1981; Bach, B. R., Arthroscopy-Assisted Patellar Tendon Substitution for Anterior Cruciate Ligament Insufficiency, America Journal of Knee Surgery, Vol. 2, No. 1 (1989), at 3–20, the entire disclosures of which are incorporated herein by way of this reference.

Rigid fixation of the ACL graft has been recognized as one of the most important factors that determine the long term success of an ACL replacement. See, e.g., Daniel D M: Principles of knee ligament surgery, in Daniel D M, Akeson W, O'Connor (eds): Knee Ligaments Structure, Function, Injury, and Repair. New York, Raven Press, 1990, pp 11–30; and Kurosoka M, Yoshiya S, Andrish J T: A Biomechanical comparison of different surgical techniques of graft fixation in anterior cruciate ligaments reconstruction, Am. J. Sports Med. 15:225–229, 1987, the entire disclosures of which are incorporated herein by way of this reference. Moreover, S. Rupp et al. made biomechanical studies of the fixation strength and the failure modes of a biodegradable screw and the press-fit fixation technique compared with a titanium interference screw in the porcine knee using a BPTB-graft. See Rupp, S., Krauss, P. W. and Fritsch, E. W., Fixation Strength of a Biodegradable Interference Screw and a Press-Fit Technique in Anterior Cruciate Ligament Reconstruction With a BPTB Graft, The Journal of Arthroscopic and Related Surgery, Vol. 13, No 1 (1997), 61–65, the entire disclosure of which is incorporated herein by way of this reference. In the study of Rupp et al., the following ultimate failure mean loads were obtained:

biodegradable screw 805.2 N titanium screw 768.6 N press-fit 462.5 N

Using screws as fixation implants of bone grafts in a bone-tendon-bone procedure is complicated by several facts:

if the threads are not cut into the drillhole, substantial compacta ossium (cortex) has to be cut off before the insertion of the absorbable screw, which (cutting of cortex) delays the surgical operation, increases trauma and can reduce the grip of the screw into the bone wall of the drillhole because, in such a case, the screw is fixed only into the mechanically weaker substantial spongiosa ossium;

when using bioabsorbable screws with the drillhole threading technique, the threading of the drillhole delays surgical operation;

the threads of the screw can cut the bone block to pieces during screw installation if the screw is too big in relation to the bone block and/or if the space between the drillhole and bone block is too small;

the threads of the screw can damage the tendon during screw installation;

the bone block (and the tendon) can rotate with the screw during screw installation so that the optimal position of the bone graft is lost and/or the bone graft is damaged;

divergence of the graft and/or screw can occur;

the bioabsorbable screw can break during insertion;

if subsequent surgery is necessary, a metal screw can potentially complicate subsequent surgery and a hardware removal may be necessary, see Rupp et al., supra; and a metal screw can disturb postoperative MRI scans, see Rupp et al., supra.

Complications, like those recited above and others, are illustrated in, e.g. in Bach et al., Barber et al. and Rupp et al., all supra. In addition, when using the prior art implants described above, the bone block must be located into the drill hole before the installation of the screw and the bone block must be kept in a proper place in the drill hole during the screw insertion. These procedures lengthen and complicate the surgical procedure.

Thus, it would be advantageous to have a bone-tendon-bone fixation implant which must not be turned into the drillhole as the prior art screws need. It would be especially advantageous to have an implant which is manufactured of bioabsorbable polymer, copolymer, polymer alloy or fiber-reinforced or particle-filled bioabsorbable polymer composite, which implant can be pushed into a hole or drill canal made into a bone, to fixate a bone graft into the drillhole.

U.S. patent application Ser. No. 08/914,137, entitled "Bone Block Fixation Implant," describes a bioabsorbable implant (bolt or wedge). This implant, which is aimed for fixation of a BPTB-graft, can be pushed into a drillhole in a bone, and comprises: (1) at least an elongated body, (2) at least one gripping element to lock the implant into the drillhole and (3) a platform surface for location of a bone block between the implant and the wall of the drillhole. The implant may be equipped with (4) an additional arresting means to prevent the slipping of the bone block out of the drillhole. However, this implant has certain limitations that are overcome by the present invention, namely:

the tendon of the bone block is not protected or the space reserved for the tendon is very limited, so that during insertion or after it, the tendon may rub against the rim of the drillhole in the bone and be damaged;

the limited space available for the tendon may result in a relatively thin and weak tendon graft;

the size of the drillhole in relation to the size of the implant must be exact because the implant is rigid and, as a result, an implant that is too large may break the bone graft, while an implant that is too small may yield a weak fixation; and the size of the bone block is small, because the wedge-like implant needs a lot of space inside of a drillhole.

Therefore, it would be advantageous to have a bone-tendon-bone fixation implant which is simple to insert and which could be used without the cutting of cortex and/or the threading of a drillhole, and which need not be turned into the drillhole as the prior art screws are. It also would be advantageous to have a bone-tendon-bone fixation implant that has a geometric configuration such that the implant slips easily into the drillhole, but exhibits strong resistance to be pulled out of the drill hole. It would also be desirable to provide an implant for fixing a bone-tendon-bone graft into a bone, which implant does not interfere with noninvasive examinations such as radiographs, MRI (magnetic resonance imaging) or CT (computer topography) and which is biocompatible, and which makes a strong and rigid fixation of a bone block in a BPTB-fixation operation.

By utilizing the present invention, it is possible, when inserting a fixation implant into a patient, to eliminate the above-mentioned difficulties and functional restrictions present in connection with prior art screws, bolts or wedges for bone-tendon-bone fixation.

BRIEF DESCRIPTION OF THE INVENTION

The present invention surprisingly discloses that the problems of the prior art can be eliminated to a great extent with a surgical fixation implant of the present invention. Thus, there is described an implant manufactured of a bioabsorbable polymer, copolymer, polymer alloy or fiber-reinforced or particle-filled bioabsorbable polymer composite, which implant is pushed into a hole or drill canal made into a bone, to fix a bone graft into the drillhole, the implant comprising: (1) at least a pliable (expandable and compressible) body, wherein the implant body comprises at least one groove formed on the surface of the implant body in the longitudinal direction of the implant body, which groove opens into (2) a fish-tail like slot inside of which part of the tendon of the BPTB-graft will be located, (3) two ailerons, formed by the walls of the implant on both sides of the slot, (4) at least one gripping element to lock the implant into the drillhole, and (5) a curved and/or slanting threshold surface to prevent the slipping of the bone block out of the drillhole. The implant may be equipped optionally with a (6) finger sleeve for fixing a bone block tightly to the implant.

BRIEF DESCRIPTION OF THE FIGURES

The invention is illustrated through the following specification, with reference made to the accompanying drawings. In the drawings:

FIG. 1 shows as figures (A–E) one embodiment in accordance with the invention.

FIG. 1A shows, as a longitudinal figure, the groove edge of the implant.

FIG. 1B shows, as a transverse figure, the non-leaning edge of the implant.

FIG. 1C shows, as a transverse figure, the leaning edge of the implant.

FIG. 1D shows, as a side view, the implant with a bone block.

FIG. 1E shows the implant with a bone block, as a longitudinal cross-sectional figure in plane a—a of FIG. 1A.

FIG. 2 shows as FIGS. (A–E) another embodiment of the implant.

FIG. 2A shows, as a longitudinal figure, the groove edge of the implant.

FIG. 2B shows, as a transverse figure, the non-leaning edge of the implant.

FIG. 2C shows, as a transverse figure, the leaning edge of the implant.

FIG. 2D shows, as a side view, the implant with a bone block.

FIG. 2E shows the implant with a bone block, as a longitudinal cross-sectional figure in plane a—a of FIG. 2A.

FIG. 3 shows, as an enlarged perspective figure, two implants equipped with ridge-like gripping elements.

FIG. 4 shows, as an enlarged perspective figure, an implant with a hole for the tip of an installation instrument.

DETAILED DESCRIPTION OF THE INVENTION

FIGS. 1A through 1E illustrate a fixation implant in accordance with the invention. Specifically, the fixation implant of the present invention comprises: (a) a cylindrical and/or conical body 1, which is pliable and which may be elongated (the length of the body can be bigger that its maximum diameter); (b) at least one gripping element 2, which locks the implant into the drillhole 3 in the bone 4 so that the gripping element(s) sink at least partially inside of the bone 4 during the insertion of the implant; (c) at least one groove 5 formed on the surface of the implant body in the longitudinal direction of the implant body; (d) a slot 6 into which the groove 5 expands and into which slot 6 a part of the tendon 7 of the BPTB-graft is located between the implant and the surface of the drillhole; (e) walls of the implant, which form ailerons (10, 11) on both sides of the slot 6, which ailerons press against the walls of the drill hole during the insertion procedure; and (f) a threshold surface 8, which typically is curved and/or slanting, which threshold surface 8 prevents the slipping of the bone block 9 out of the drillhole after insertion, but which also serves to guide the bone block 9 to partly protrude into the slot 6 during the insertion procedure to expand the implant by pressing the ailerons or wings (10, 11) against the walls of the drillhole. According to one advantageous embodiment of the present invention, the cross-sectional form of the slot 6 is fish-tail like, so that the tendon is protected securely inside of the slot against damage, both during the insertion procedure and after it.

Additionally, according to FIG. 2, the implant 1 can include a finger-sleeve 16 on which the bone graft 9 (from which the tendon 7 emerges) is located between the implant 1 and the surface of the drillhole 3. The finger-sleeve 16 of the implant 1 can include at least one hole 12. The bone graft may be fixed on the implant by means of tied suture(s) 13, which go through the finger-sleeve hole 12 and through a hole 14 made into the bone block. The sutures 13 can also be tied around the bone block and/or around the finger-sleeve 16. A tight press fit of implant 1 and bone graft (block) 9 into the drillhole 3 is achieved when the maximum thickness of the implant 1 combined with the maximum thickness of the bone graft 9 is larger than the diameter of the drillhole 3.

Referring still to FIGS. 1 and 2, it is seen that the implant of the invention comprises a groove 5 and a slot 6 for the tendon. The groove 5 and the slot 6 protect the tendon 7 and provide the implant body 1 with expansion capacity after its insertion. That expandability and compressibility (pliability) of the implant of the present invention makes inserting of the implant simpler and easier than if the implant were stiff. Moreover, under the present invention, after the pliable implant is inserted into the drillhole, it expands to the walls of the drillhole and resists being removed from the drillhole.

FIGS. 1E and 2E show typical longitudinal cross-sections of the implants with a bone block 9, located into the drillhole 3 in the bone. Accordingly, most advantageously, the outer surface of the implant 1 is cylindrical of its form and the gripping elements 2 are formed on the cylindrical surface of the implant.

The gripping elements 2 illustrated in FIGS. 1 and 2 are typically protuberances emerging from the surface of the implant. Such protuberances are, e.g,. threads, barbs or transverse ridges. The geometry of gripping elements is such that the implant 1 slips easily into the drillhole 3, but does not slip back again after its insertion. According to the advantageous embodiments of the invention depicted in FIGS. 1–3, the gripping elements are transverse ridges 2 emerging from the surface of the implant 1. The ridges 2 according to FIG. 3 cause only a little resistance when the implant 1 with the bone graft is pushed into the drillhole, but the ridges effectively prevent the slippage of the implant 1 back from the drillhole 3 after its insertion. Because the bone graft is locked into the drillhole in relation to the implant, any potential slippage of the bone graft back from the drillhole is also effectively prevented. Many additional geometries for the gripping elements (like barbs or threads) of the implant of the invention can be used to achieve the same results, as would be apparent to persons of ordinary skill in the art.

FIG. 3 shows as perspective figures two typical implants of the invention, each having circular ridges as gripping elements 2 around the cylindrical body of the implant, with a threshold surface 8 and with a finger sleeve 16.

The implant of the invention can be pushed arthroscopically into a drillhole in a bone, with the bone block fixed on the finger-sleeve 16, using, e.g., one or a combination of the following techniques:

the implant of the invention (with the fixed bone block) is pushed to its place through a tube-like cannula;

a longitudinal hole is made through the implant for receipt of a guide wire, and the implant (and fixed bone block) is pushed into its place in the drillhole along the guide wire; and a small, (optionally threaded) hole or notch 15 (see FIGS. 1B, 2B and 4) is made in the proximal part of the implant, so that the tip of a (e.g, bayonet-like) installation instrument is fixed (pushed) into the hole (15), and the instrument is used to push the attached implant (and fixed bone block) into position in the drillhole; and a small, transverse hole 12 (see FIG. 2A) is made through the finger-sleeve of the implant for a suture 13 and the implant (and fixed bone block) is pushed into place using the suture to control the positioning of the bone block.

Alternatively, the bone block can be inserted into the drillhole prior to the implant. In that case (where the bone block is first inserted into the drillhole, followed by the implant), the bone block can be pushed arthroscopically into the drillhole in the same manner as described above for the implant.

By inserting implants according to the invention, it is possible to efficiently attach and immobilize bone grafts into drillholes in bone, against forces tending to loosen the bone grafts, without having to carry out a time-consuming and risky fixations with a screw or other prior art implant, which fixations may damage the bone block and/or the tendon graft fixed to the bone graft. Fixation implants in accordance with the invention can be manufactured of bioabsorbable (biodegradable or resorbable) polymers, copolymers, polymer alloys or composites, e.g., of poly-α-hydroxide acids and other aliphatic biodegradable polyesters, polyanhydrides, polyorthoesters, polyorganophosphatsenes and other bioabsorbable polymers known in the art and disclosed in numerous publications, e.g., in Vainionpää, S., Rokkanen, P. and Törmälä, P. Surgical Applications of Biodegradable Polymers in Human Tissues, Progr. Polym. Sci., Vol. 14, (1989), at 679–716, as well as in Finnish Patent Applications FI-952884, FI-955547 and the publication WO-90/04982, the entire disclosures of which are incorporated herein by way of this reference.

Implants in accordance with the invention can be manufactured of biodegradable polymers by using one polymer or polymer alloy. The implants can also be reinforced by reinforcing the material by fibres manufactured of resorbable polymer or polymer alloy, or biodegradable glass fibers, such as β-tricalsiumphosphate fibres, bio-glass fibers or CaM fibres (see, e.g., publication EP146398, the entire disclosure of which is incorporated herein by way of this reference). Ceramic powders can also be used as additives (fillers) in implants to promote new bone formation.

Implants according to the invention can also comprise a flexible outer layer, which is a surface layer improving the toughness of the implant and/or operating as a hydrolysis barrier, and a stiffer inner layer or core of the implant. To prepare such an embodiment, the implant can be coated with an outer layer having different chemical and mechanical properties (e.g., hydrolysis and strength retention) than the core of the implant. In such a case, an outer layer having greater resistance to hydrolysis than the implant's core can be used, enabling the implant (after insertion in a patient) to retain its strength and biodegrade in less time than it would have without such an outer coating.

Surgical implants in accordance with the invention can be manufactured of biodegradable polymers, which may or may not contain suitable biodegradable reinforcement fibres and/or particle fillers, by means of various methods used in plastic technology, such as injection molding, extrusion and fibrillation and molding related thereto (see, e.g., U.S. Pat. No. 4,968,317, the entire disclosure of which is hereby incorporated by reference) or by means of compression molding, wherein the implants are shaped from the raw material by employing heat and/or compression. Also mechanical machining (e.g., cutting, drilling, lathing, grinding etc.) can be used to prepare the implants of the present invention.

According to one advantageous embodiment of the invention, the implant contains holes or open porosity to facilitate tissue (such as bone) growth inside of the implant. Such holes or pores typically have a diameter from 100 $\mu$m to 2000 $\mu$m. The holes or pores may be filled at least partially with cancellous bone of the patient or with ceramic bone substitute powder or granules (like bioactive glass), to accelerate their filling with new bone. The growth of such new bone inside of the holes or pores of the implant facilitates the final healing of the drillhole and the fixation of bone block inside of the drillhole, when the implant biodegrades and disappears from the drillhole.

It also is possible to manufacture implants of the invention using the aforementioned polymeric raw materials in dissolving techniques, which are known in the art. Under such techniques, at least part of the polymer is either dissolved in a suitable solvent or softened by means of that solvent; the polymer is then compressed into an implant piece by means of pressure and/or by means of slight heat, wherein the dissolved or softened polymer is glued to form a macroscopic implant piece, wherefrom the solvent is removed by evaporation.

It is natural that the implants of the invention can also contain various additives for facilitating the processability of the material (e.g., stabilizers, antioxidants or plasticisers) or for changing its properties (e.g., plasticisers or ceramic powder materials or biostable fibres, such as carbon fibres) or for facilitating its treatment (e.g. colorants).

According to one advantageous embodiment, the implant of the invention contains some bioactive agent or agents, such as antibiotics, chemotherapeutic agents, agents activating healing of wounds, growth factor(s), bone morphogenic protein(s), anticoagulant (such as heparin) etc. Such bioactive implants are particularly advantageous in clinical use, because they have, in addition to their mechanical effect, also biochemical, medical and other effects to facilitate tissue healing and/or regeneration.

The invention and its function is further illustrated by way of the following examples.

EXAMPLE 1

The aim of this example was to demonstrate how the diameter of the implant body in relation to the diameter of the drillhole in the bone affects the fixation strength of the implant.

Implants in accordance with FIG. 2. were manufactured with a length of 22 mm (including a 12 mm long finger-sleeve) and having variable diameters from 10.3 mm to 10.8 mm.

In this example, each implant with one end of a trimmed BPTB-graft was inserted into a drill hole of 10 mm in diameter, which was made through the femoral metaphyseal bone of pig using a cannulated drill. The bone was fixed into the lower jaw of a tensile testing machine (Lloyd LR5K, available from J J Lloyd Instruments, Southampton, UK). After fixing the other end of the BPTB-graft into the upper (moving) jaw of the tensile testing machine, the BPTB-graft, which was fixed with the implant into the drillhole, was subjected to a vertical tensile loading at a strain rate of 50 mm/min, until failure. Two samples were tested in each case. Table 1 gives the measured forces for failure for each of the tested implants.

TABLE 1

| Max. Diameter of Implant (mm) | Force to failure (N) Sample 1 | Force to failure (N) Sample 2 |
| --- | --- | --- |
| 10.3 | 607 | 358 |
| 10.4 | 201 | 142 |
| 10.5 | 370 | 287 |
| 10.6 | 1312 | 686 |
| 10.7 | 777 | 1298 |
| 10.8 | 1427 | 1228 |

This test showed that through the selection of the proper diameter of the implant of the invention, the force to failure values of the implant of the invention are superior to those reported in literature for prior art interference screws (768.6 N; and a range of 544 to 1094 N, reported in Daniel D M: Principles of knee ligament surgery, in Daniel D M, Akeson W, O'Connor (eds): Knee Ligaments Structure, Function, Injury, and Repair. New York, Raven Press, 1990, pp. 11–30).

EXAMPLE 2

The aim of this example was to demonstrate how rapid and simple the implant is to operate and how secure the fixation of the implant is. The fixation capacity of a biodegradable implant in accordance with the invention (diam. of 10.8 mm) was compared with the performance of a titanium interference screw (Acufex; available from Acufex Microsurgical Inc, Mansfield, Mass.; diam. 7 mm, length 25 mm) and fixation implants made in accordance with U.S. patent application Ser. No. 08/914,137 (wedges with the following dimensions: length 25 mm, width 10 mm and height of the ridged implant body 7 mm) in an anterior cruciate ligament (ACL) reconstruction, using a bone-patellar-tendon-bone (BPTB) graft in the porcine knee. The same test methods were used as in Example 1. Again, two parallel tests were carried out in each case. Table 2 gives the measured forces for failure.

TABLE 2

| Implant | Force to failure (N) Sample 1 | Force to failure (N) Sample 2 |
| --- | --- | --- |
| Present Invention | 1228 | 1427 |
| Interference screw | 349 | 975 |
| Wedge of US Pat. Appl. No. 08/914,137 | 770 | 921 |

The results indicate that the biodegradable implant of the present invention provides a more stable graft fixation than the prior art implants. This test also showed that, in accordance with the disclosure above, inserting of the implant of the present invention is easier and swifter, and it protects the BPTB graft better during operation than the prior art fixation implants.

We claim:

1. A surgical implant for fixing a bone block into a drillhole in a bone, said implant comprising: at least one elongated body having walls and manufactured from bioabsorbable polymer, copolymer, polymer alloy or composite; at least one gripping element on the elongated body, for locking the implant into the drillhole; at least one slot on the elongated body; two ailerons formed by the walls of the elongated body; and a curved or slanting threshold surface on the elongated body, to prevent the bone block from slipping out of the drillhole.

2. A surgical implant according to claim 1, further comprising a finger-sleeve on the elongated body, for locating the bone block rigidly on the implant.

3. A surgical implant according to claims 1, wherein said slot has a fish-tail like cross-section.

4. A surgical implant according to claim 1, wherein said at least one gripping element comprises at least one protuberance.

5. A surgical implant according to claim 1, wherein said at least one gripping element comprises at least one thread.

6. A surgical implant according to claim 1, wherein said at least one gripping element comprises at least one transverse ridge.

7. A surgical implant according to claim 1, wherein said at least one gripping element comprises at least one barb.

8. A surgical implant according to claim 1, wherein said elongated body is cylindrical in form.

9. A surgical implant according to claim 1, wherein said elongated body is porous.

10. A surgical implant according to claim 1, wherein said implant is capable of releasing a drug or other bioactive substance.

11. A method of inserting the surgical implant of claim 1 and a bone block into a drillhole in a bone, comprising the steps of:
   a. attaching the bone block to the elongated body;
   b. inserting the bone block and elongated body into the drillhole; and
   c. locking the implant into the drillhole by means of the gripping means on the implant.

12. A method of inserting the surgical implant of claim 1 and a bone block into a drillhole in a bone, comprising the steps of:
   a. inserting the bone block into the drillhole;
   b. inserting the elongated body into the drillhole;
   c. locking the implant into the drillhole by means of the gripping means on the implant.

* * * * *